US012070210B2

(12) United States Patent
Liu et al.

(10) Patent No.: US 12,070,210 B2
(45) Date of Patent: Aug. 27, 2024

(54) BENDABLE ENDOSCOPIC LINEAR CUTTING ANASTOMAT AND ASSEMBLY THEREOF

(71) Applicant: B. J. ZH. F. PANTHER MEDICAL EQUIPMENT CO., LTD., Beijing (CN)

(72) Inventors: Qing Liu, Beijing (CN); Hongli Fan, Beijing (CN); Zhanchuan Huang, Beijing (CN)

(73) Assignee: B. J. ZH. F. PANTHER MEDICAL EQUIPMENT CO., LTD., Beijing (CN)

( * ) Notice: Subject to any disclaimer, the term of this patent is extended or adjusted under 35 U.S.C. 154(b) by 22 days.

(21) Appl. No.: 17/800,507

(22) PCT Filed: Jan. 11, 2021

(86) PCT No.: PCT/CN2021/071122
§ 371 (c)(1),
(2) Date: Aug. 17, 2022

(87) PCT Pub. No.: WO2021/169634
PCT Pub. Date: Sep. 2, 2021

(65) Prior Publication Data
US 2023/0078358 A1 Mar. 16, 2023

(30) Foreign Application Priority Data
Feb. 27, 2020 (CN) .......................... 202010123631.8

(51) Int. Cl.
*A61B 17/072* (2006.01)
(52) U.S. Cl.
CPC ............... *A61B 17/07207* (2013.01); *A61B 2017/07221* (2013.01); *A61B 2017/07264* (2013.01);
(Continued)

(58) Field of Classification Search
CPC ............. A61B 17/068; A61B 17/2816; A61B 17/07207; A61B 17/00234;
(Continued)

(56) References Cited

U.S. PATENT DOCUMENTS 1,413,291 A * 4/1922 Overshiner ............. B29C 73/04
152/196
5,312,023 A * 5/1994 Green ............... A61B 17/07207
227/19
(Continued)

FOREIGN PATENT DOCUMENTS

| CN | 205339036 U | 6/2016 |
| CN | 107708578 A | 2/2018 |
| CN | 212661858 U | 3/2021 |

OTHER PUBLICATIONS

International Search Report issued in International Patent Application No. PCT/CN2021/071122; China National Intellectual Property Administration (ISA/CN), Beijing, China, mailed Apr. 9, 2021; 8 pgs.
(Continued)

*Primary Examiner* — Stephen F. Gerrity
*Assistant Examiner* — Linda J Hodge
(74) *Attorney, Agent, or Firm* — HAUPTMAN HAM, LLP

(57) ABSTRACT

A bendable endoscopic linear cutting anastomat and assembly includes an anastomat jaw, a turning connection block, an assembly inner core and a cutting blade assembly. The assembly inner core includes an inner core shell and an inner core connection block fixedly mounted in the inner core shell. The front end of the turning connection block is hinged to the rear end of the anastomat jaw, a first vertical rotation shaft is formed at the hinge, the rear end of the turning connection block is hinged to the front end of the inner core connection block, a second vertical rotation shaft is formed
(Continued)

at the hinge; the cutting blade assembly penetrates through the inner core connection block, the turning connection block and the anastomat jaw, and can slide forwards and backwards. As a result, a U-shaped left and right bending sheet which controls the bending process.

10 Claims, 5 Drawing Sheets

(52) U.S. Cl.
CPC .............. *A61B 2017/07271* (2013.01); *A61B 2017/07285* (2013.01)

(58) Field of Classification Search
CPC ........... A61B 2017/00232; A61B 2017/00327; A61B 2017/2908; A61B 2017/2917; A61B 2017/07221; A61B 2017/07264; A61B 2017/07271; A61B 2017/07285; A61B 1/008

See application file for complete search history.

(56) References Cited

U.S. PATENT DOCUMENTS

| | | | |
|---|---|---|---|
| 2003/0233066 A1* | 12/2003 | Ewers ................ | A61B 1/00105 604/27 |
| 2011/0295063 A1* | 12/2011 | Umemoto ............ | A61B 1/0057 600/109 |
| 2018/0289372 A1* | 10/2018 | Nie ....................... | A61B 17/295 |
| 2019/0029767 A1* | 1/2019 | Hasegawa .............. | A61B 34/30 |
| 2020/0345209 A1* | 11/2020 | Whitney ............... | A61B 1/0052 |

OTHER PUBLICATIONS

Written Opinion of the International Searching Authority issued in International Patent Application No. PCT/CN2021/071122; Beijing, China, mailed Apr. 9, 2021; 8 pgs.

* cited by examiner

BENDABLE ENDOSCOPIC LINEAR CUTTING ANASTOMAT AND ASSEMBLY THEREOF

RELATED APPLICATIONS

The present application is a U.S. National Phase of International Application Number PCT/CN2021/071122, filed Jan. 11, 2021, and claims priority to Chinese Application Number 202010123631.8, filed Feb. 27, 2020.

FIELD

The present invention relates to the field of medical devices, and in particular to a bendable endoscopic linear cutting anastomat and assembly thereof.

BACKGROUND

An endoscopic anastomat plays the most critical role in surgery. Due to the limitation of the space inside the abdominal cavity or the thoracic cavity, the traditional linear endoscopic anastomat cannot completely and effectively reach the required surgical site for clamping, transversely cutting and anastomosing tissues, therefore an elbow anastomat in which an anastomat jaw (comprising a staple cartridge assembly, a stapler anvil) can be bent is required. In the linear state, the bendable elbow anastomat enters into the thoracic cavity or the abdominal cavity by a trocar, and the anastomat jaw is controlled to be bent to a certain angle by the control bending mechanism on the handle outside the body, and a series of operations such as clamping, transversely cutting and anastomosing are performed on the surgical site. After the surgery is completed, the anastomat is changed to a linear state again and is taken out of the body.

When the endoscopic linear cutting anastomat and assembly thereof are operated to perform a surgery, the anastomat jaw of the assembly is controlled to bend leftwards and rightwards by manipulating the turning control structure on the endoscopic linear cutting anastomat, so that the body positions of different surgical environments are completed. As shown in FIG. 1, the endoscopic linear cutting anastomat assembly in the prior art comprises an anastomat jaw 1, an assembly inner core 2, a turning connection rod 3, the anastomat jaw 1 is rotatably connected with the assembly inner core 2 by an upper rotation head assembly 4, an upper and lower connection sheet 5, and pushing or pulling the turning connection rod 3 with hand assistance by the connection of a head end hole 31 of the turning connection rod 3 and a turning knob pin 41 of the upper rotation head assembly 4 makes the anastomat jaw 1 at the front end of the assembly swing left and right around the rotation shaft to form bending of up to 45 degrees left and right respectively, as shown in FIGS. 2 and 3. In the above-mentioned structure, when in a bending state, firing and cutting and anastomosing require a larger firing force, which affects the doctor's operation hand feeling. In addition, the left and right swing angles of the anastomat jaw are limited, such that a series of operations such as partial surgical clamping, transversely cutting and anastomosing cannot reach an ideal operation position, and cannot be suitable for medical treatment under more complex clinical conditions.

SUMMARY

The technical problem to be solved by the present invention is to provide a bendable endoscopic linear cutting anastomat and assembly thereof, which can reduce the firing force during cutting and anastomosing, and can increase the bending angle, so as to enable a doctor to have a better operation hand feeling and operation space.

In order to solve the above-mentioned technical problem, the present invention adopts the following technical solution:

A bendable endoscopic linear cutting anastomat assembly, comprising an anastomat jaw, a turning connection block, an assembly inner core and a cutting blade assembly; the assembly inner core comprises an inner core shell and an inner core connection block fixedly mounted in the inner core shell; a front end of the turning connection block is hinged to a rear end of the anastomat jaw, a first vertical rotation shaft is formed at the hinge, a rear end of the turning connection block is hinged to a front end of the inner core connection block, a second vertical rotation shaft is formed at the hinge; the cutting blade assembly penetrates through the inner core connection block, the turning connection block and the anastomat jaw, and can slide forwards and backwards.

As a further improvement of the present invention, further comprising a left and right bending sheet and a push-pull rod; the left and right bending sheet is U-shaped, a bending part of a rear part of the left and right bending sheet turns by the inner core connection block, and two free ends at a front end of the left and right bending sheet penetrate through the turning connection block from the rear to the front and are then fixedly connected to the rear end of the anastomat jaw; a left side or a right side of the left and right bending sheet is connected to a front end of the push-pull rod, and can drive the anastomat jaw to bend left and right around the first vertical rotation axis and the second vertical rotation axis under the push-pull action of the push-pull rod.

Further, the anastomat jaw comprises a staple cartridge assembly located at the upper part and a stapler anvil connected to the staple cartridge assembly and located at the lower part, and further comprises a stapler anvil positioning piece located at the inner side of a rear part of the stapler anvil; the free ends of the left and right bending sheet are fixedly connected between the stapler anvil positioning piece and the rear part of the stapler anvil via a transversely connected pin, and the cutting blade assembly penetrates through the stapler anvil positioning piece.

Further, the turning connection block is connected to a positioning block connection shaft provided on the stapler anvil positioning piece via a vertical positioning block connection hole provided at the front end of the turning connection block; the turning connection block is connected to an inner core connection shaft provided at the front end of the inner core connection block via a vertical inner core connection block positioning hole provided at the rear end of the turning connection block.

Further, the cutting blade assembly comprises a cutting blade assembly upper sheet and a cutting blade assembly lower sheet, and the cutting blade assembly upper sheet and the cutting blade assembly lower sheet respectively and sequentially penetrate through the inner core connection block, the turning connection block, and the upper part and the lower part of the stapler anvil positioning piece, and are connected into one piece at a front end of the cutting blade assembly.

Further, a rear end of the inner core connection block is provided with a U-shaped groove, and an inner side of the bending part of the left and right bending sheet is fitted with the U-shaped groove.

Further, a plurality of protruding snap-position steps are respectively provided on an upper surface and a lower surface of the inner core connection block, and an accommodating space for the cutting blade assembly upper sheet or the cutting blade assembly lower sheet is respectively formed among the plurality of protruding snap-position steps; the inner core shell comprises an inner core upper cover and an inner core lower cover, and the inner core connection block is connected to the inner core upper cover and the inner core lower cover by a snap-position step.

Further, a left side face and a right side face of the turning connection block are respectively provided with a left and right bending sheet penetration opening, and a connection end of the push-pull rod and the left and right bending sheet is located at a rear end of the left and right bending sheet penetration opening; the anastomat assembly further comprises a push-pull block, the push-pull rod is fitted into a push-pull block hole provided at a rear part of the push-pull block by a fixing boss provided at a front part of the push-pull rod, the push-pull block is fitted into a fixing hole provided at the left side or the right side of the left and right bending sheet via a push-pull block shaft provided at a front part of the push-pull block.

Further, the bending part of the rear of the left and right bending sheet is replaced by a flexible steel wire rope, and the flexible steel wire rope and a front part of the left and right bending sheet are press-fitted by a connection ring; or the left and right bending sheet is completed replaced with the flexible steel wire rope.

The present invention also provides a bendable endoscopic linear cutting anastomat assembly, comprising a handle and a bendable endoscopic linear cutting anastomat assembly connected to a front end of the handle, the bendable endoscopic linear cutting anastomat assembly adopts the above-mentioned bendable endoscopic linear cutting anastomat assembly.

By adopting the above-mentioned technical solution, the present invention has at least the following advantages:

1. According to the present invention, the dual rotation centers are adopted, so that a large bending radius of a cutting blade can be achieved, the firing force during use is effectively reduced, and a doctor obtains a better operation hand feeling. In addition, the bending radius can be increased, and a larger bending angle can be achieved, so that a doctor has a better operation space, and is suitable for medical treatment under more complex clinical conditions.

2. In the present invention, a flexible left and right bending sheet is used to continuously maintain the left and right bending to be a pulling process by reversing, thereby preventing a force arm from being reduced during the bending process, the moment is stable and a larger bending angle can be achieved.

BRIEF DESCRIPTION OF THE DRAWINGS

The foregoing is only an overview of the technical solutions of the present invention. To make the technical means of the present invention clearer, the present invention is further described in detail in the following with reference to the accompanying drawings and specific embodiments.

DETAILED DESCRIPTION

Figure 1:
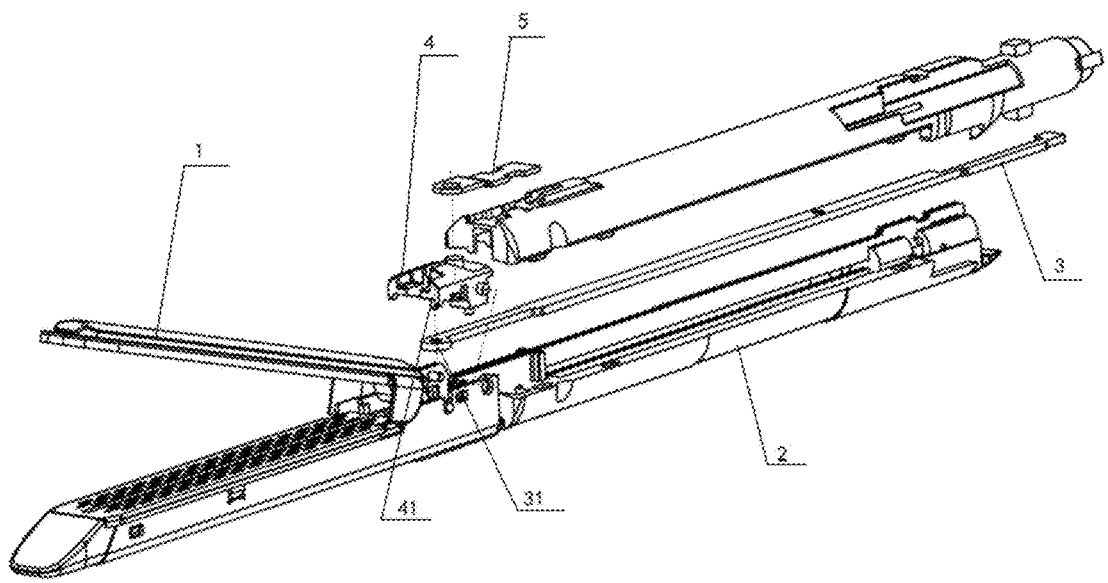
FIG. 1 is a schematic diagram of an explosion structure of an endoscopic linear cutting anastomat assembly in the prior art.
Figure 2:
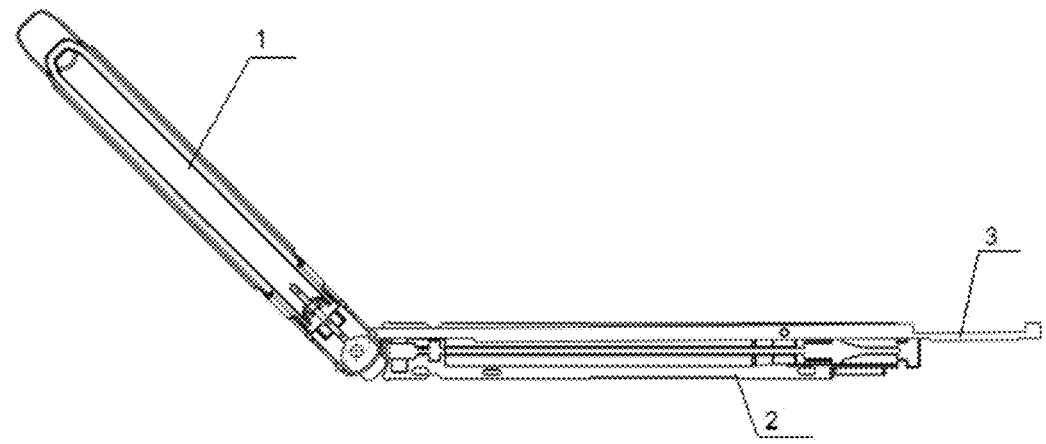
FIGS. 2 and 3 are schematic diagrams of the endoscopic linear cutting anastomat assembly in FIG. 1 being bended rightwards and leftwards respectively.
Figure 3:
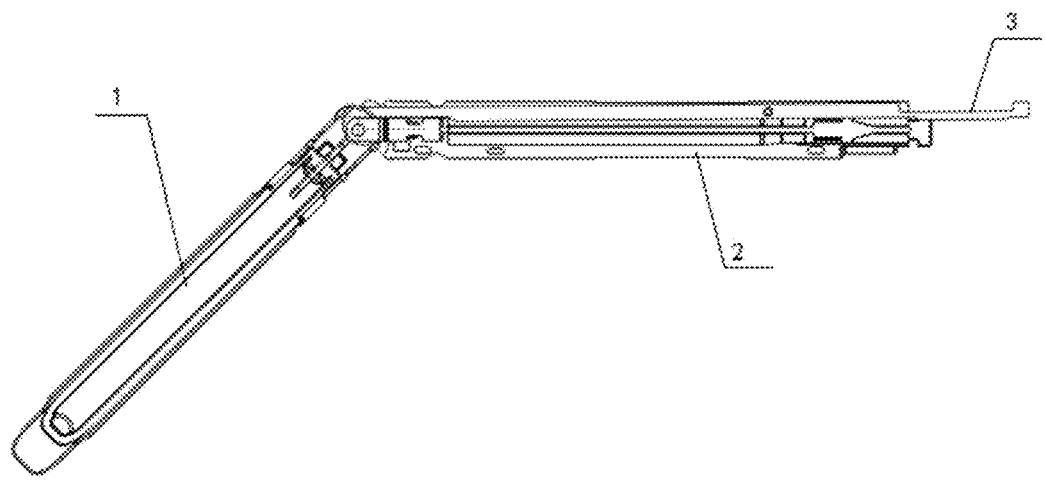
Figure 4:
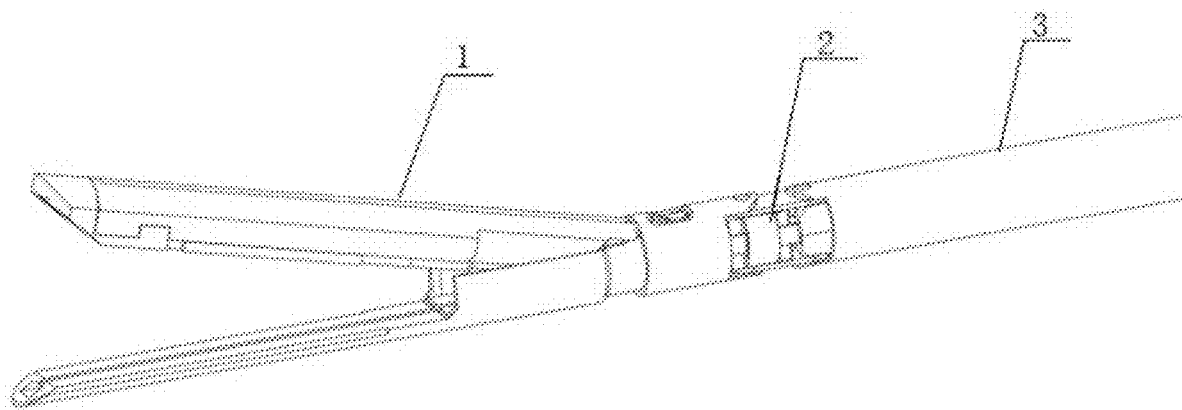
FIG. 4 is a schematic diagram of an external configuration of a bendable endoscopic linear cutting anastomat assembly according to one embodiment of the present invention.
Figure 5:
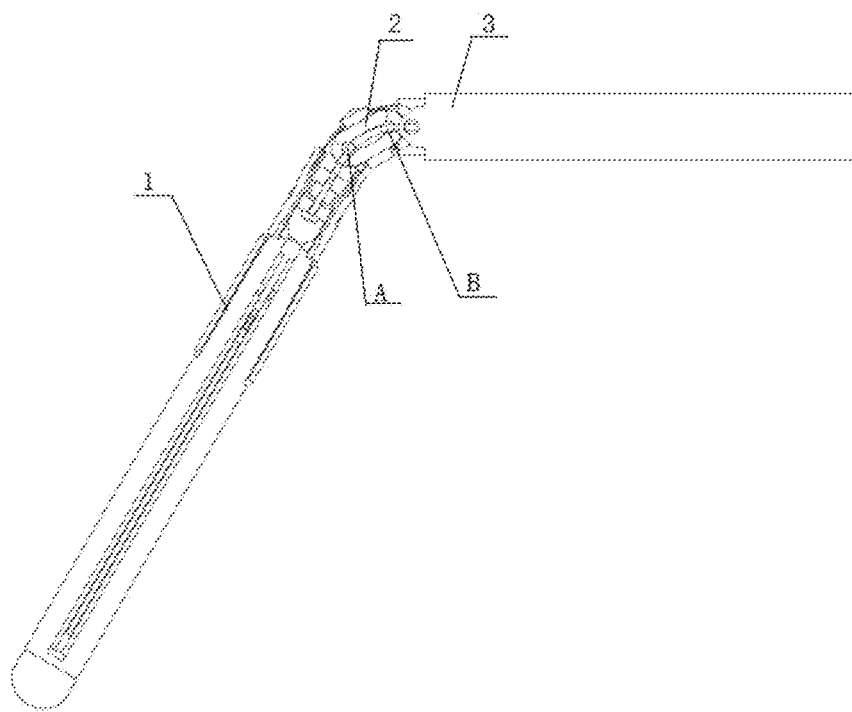
FIG. 5 is a schematic diagram of a bendable endoscopic linear cutting anastomat assembly in a bending state according to one embodiment of the present invention.
Figure 6:
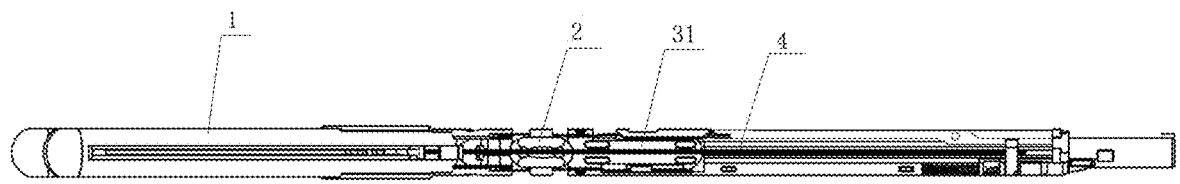
FIG. 6 is a top view structure schematic diagram of a bendable endoscopic linear cutting anastomat assembly according to one embodiment of the present invention (visible interior)

The preferred embodiments of the present invention will be described below with reference to the accompanying drawings. It should be understood that the preferred embodiments described herein are only used for describing and explaining the present invention, rather than limiting the present invention.

With regard to the following problems existing in the prior art: when the device is in a bending state, firing and cutting and anastomosing need a larger firing force, thereby affecting the doctor's operation hand feeling, and the left and right swing angle of the anastomat jaw is limited, such that a series of operations such as partial surgical clamping, transversely cutting and anastomosing, cannot reach an ideal operation position, and cannot be suitable for medical treatment under more complex clinical conditions. The applicant finds out through experiments for many times that the reason is the arrangement of the single rotation center, and the cutting blade bends along with the single rotation center in the bending process due to the fact that the single rotation center is adopted, the turning angle is too large, so that a smaller bending radius is formed in the bending process of the cutting blade, the firing force in the cutting and anastomosing process is too large, the doctor's operation hand feeling is influenced, and the fault risk of the anastomat is increased. In addition, the applicant also finds that in the existing structure, the turning connection rod is rigidly connected, the length of a force arm between the turning connection rod and the rotation shaft is limited by space, so that the left and right swing angle is limited, and a series of operations such as partial operation clamping, transversely cutting and anastomosing and the like cannot reach an ideal operation position, and the medical treatment under more complex clinical conditions cannot be realized.

Based on the above-mentioned findings, the applicant respectively makes corresponding improvements on the bending part and the bending control part in the prior art.

For ease of description, in the present invention, the anastomat jaw end is defined as front and the manipulator end is defined as rear, the opening and closing direction of the anastomat jaw is up and down, and the bending direction of the anastomat jaw is left and right. The arrangement of the above-mentioned directions is not used to limit the present invention.

As shown in FIGS. 4-7, the present embodiment provides a bendable endoscopic linear cutting anastomat assembly, comprising an anastomat jaw 1, a turning connection block 2, an assembly inner core 3 and a cutting blade assembly 4, wherein the assembly inner core 3 belongs to a shell fixing type component, comprising an inner core shell and an inner core connection block 31 fixedly mounted inside the inner core shell, a front end of the turning connection block 2 is hinged to a rear end of the anastomat jaw 1, a first vertical rotation axis A is formed at the hinge, a rear end of the turning connection block 2 is hinged to a front end of the core connection block 31, a second vertical rotation axis B is formed at the hinge; the cutting blade assembly 4 penetrates through the inner core connection block 31, the turning connection block 2 and the anastomat jaw 1 and can slide forwards and backwards.

By means of the above-mentioned arrangement, when the anastomat jaw 1 is bent, the anastomat jaw 1 can rotate around the dual rotation centers (the first vertical rotation axis A, the second vertical rotation axis B), thereby realizing a large bending radius of the cutting blade, effectively reducing the firing force during use, and enabling a doctor to obtain a better operation hand feeling. In addition, the bending radius can be increased, and a larger bending angle can be achieved, so that a doctor has a better operation space, and is suitable for medical treatment under more complex clinical conditions.

On the above-mentioned basis, in order to further solve the bending control problem, in conjunction with what are shown in FIGS. 7-11, the bendable endoscopic linear cutting anastomat assembly of the present embodiment further comprises a left and right bending sheet 5 and a push-pull rod 6. Specifically, in conjunction with what are shown in FIGS. 7, 8, 9 and 11, the left and right bending sheet 5 is U-shaped, and the rear bending part thereof turns by the inner core connection block 31. Specifically, the rear end of the inner core connection block 31 may be provided with a U-shaped groove 313, and the inner side of the bending part of the left and right bending sheet 5 may be fitted with the U-shaped groove 313. Two free ends of the front end of the left and right bending sheet 5 penetrate through the turning connection block 2 from the rear to the front and are then fixedly connected to the rear end of the anastomat jaw 1. Specifically, a left and right bending sheet penetration opening may be respectively provided on a left side face and a right side face of the turning connection block 2, and the connection end of the push-pull rod 6 and the left and right bending sheet 5 is located at rear end of the left and right bending sheet penetration opening. The left side or right side of the left and right bending sheet 5 is connected to a front end of the push-pull rod 6, and can drive the anastomat jaw 1 to bend left and right around the first vertical rotation axis A and the second vertical rotation axis B when the push-pull rod 6 is pushed and pulled.

Figure 7:
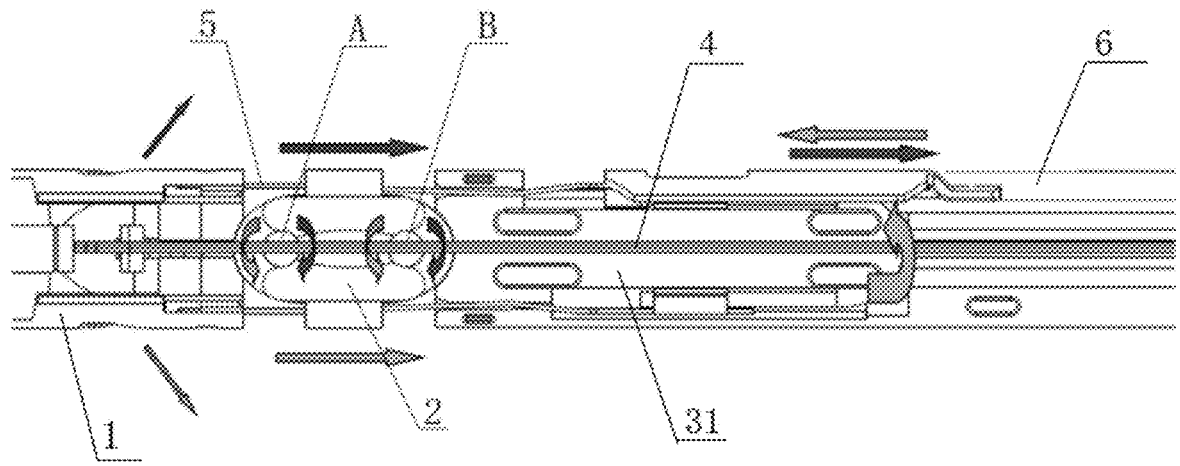
FIG. 7 is a functional diagram of a bendable endoscopic linear cutting anastomat assembly according to one embodiment of the present invention.

With reference to FIG. 7, the above-mentioned bending control process is specifically implemented in the following manner: taking an example in which the push-pull rod 6 is disposed on the right side of the left and right bending sheet 5, during operation, when the push-pull rod 6 is pushed by means of the assistance force, the push-pull rod 6 drives the right side of the left and right bending sheet 5 to move forwards, further drives the left side of the left and right bending sheet 5 to move backward, and drives the anastomat jaw 1 connected to the front end of the left and right bending sheet 5 to bend to the left around two rotation centers of the turning connection block 2. On the contrary, when the push-pull rod 6 is pulled by means of the assistance force, the push-pull rod 6 drives the right side of the left and right bending sheet 5 to move backward, further drives the left side of the left and right bending sheet 5 to move forward and drives the anastomat jaw 1 connected to the front end of the left and right bending sheet 5 to bend to the right around the two rotation centers of the turning connection block 2. Of course, what is described above is only an explanation of the operation principle of the push-pull bending of the present invention. The push-pull rod 6 may also be mounted on the left side of the left and right bending sheet 5, in which case the anastomat jaw 1 is bent to the right side by the push force and to the left side by the pull force.

In the above-mentioned push-pull process, a push-pull rod 6 fixed on one side of the left and right bending sheet 5 is applied a push force or a pull force, thereby preventing the reduction of a force arm in the bending process, the moment is stable, and a larger bending angle can be achieved.

Figure 8:
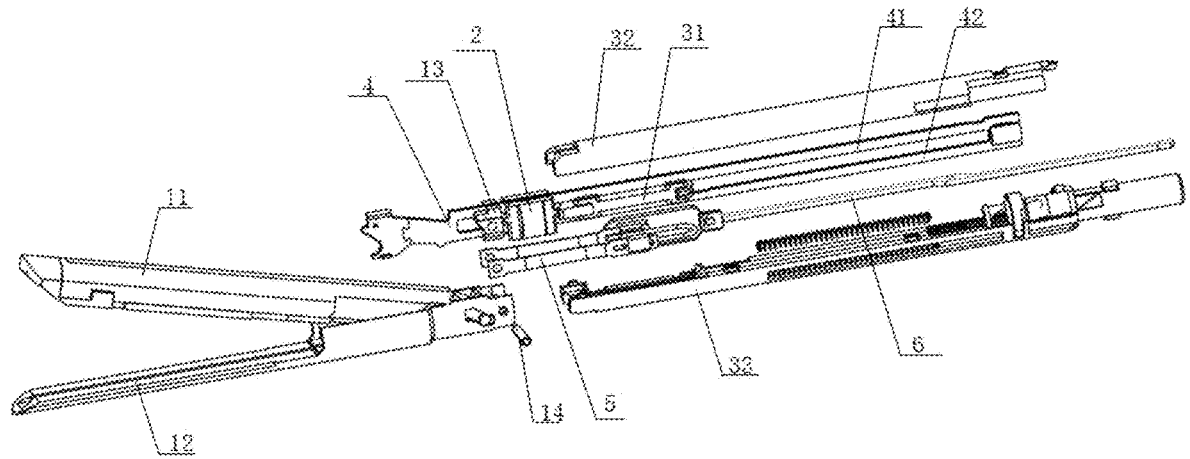
FIG. 8 is a schematic diagram of an explosion structure of a bendable endoscopic linear cutting anastomat assembly according to one embodiment of the present invention.
Figure 9:
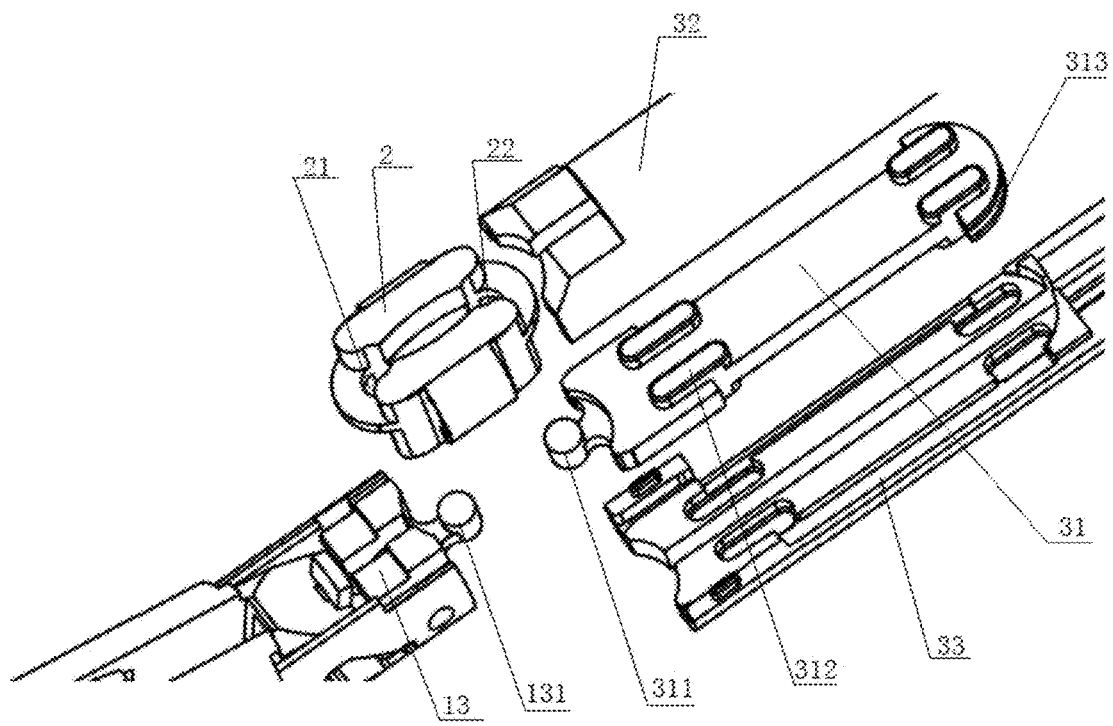
FIG. 9 is a schematic diagram of partial explosion structure of a bendable endoscopic linear cutting anastomat assembly according to one embodiment of the present invention (at the connection of the dual rotation centers)

As shown in FIGS. 8 and 9, in the connection relationship among the turning connection block 2 and the anastomat jaw 1 and the inner core connection block 31, the following structure is preferred:

a vertical positioning block connection hole 21 is provided at the front end of the turning connection block 2, and a positioning block connection shaft 131 is provided on a stapler anvil positioning piece 13 of an anastomat jaw 1 (comprising a staple cartridge assembly 11 located at the upper part, a stapler anvil 12 connected to the staple cartridge assembly and located at the lower part, and a stapler anvil positioning piece 13 located at the inner side of the rear part of the stapler anvil 12). The positioning block connection hole 21 is connected to the positioning block connection shaft 131 to form a first vertical rotation axis A; a vertical inner core connection block positioning hole 22 is provided at the rear end of the turning connection block 2, an inner core connection shaft 311 is provided at the front end of the inner core connection block 31, and the inner core connection block positioning hole 22 is connected to the inner core connection shaft 311 to form a second vertical rotation axis B.

Of course, it can be understood that a reasonably enlarged bending radius can be realized as long as the dual rotation centers can be formed. The connection relationship of the dual rotation centers in the present invention should not be limited by the above-mentioned arrangement, for example, the positions of the shafts and the holes can also be interchanged or designed to intersect.

On the basis of the stapler anvil positioning piece 13, the free ends of the left and right bending sheet 5 can be fixedly connected between the stapler anvil positioning piece 13 and the rear part of the stapler anvil 12 via a transverse connection pin 14.

Figure 10:
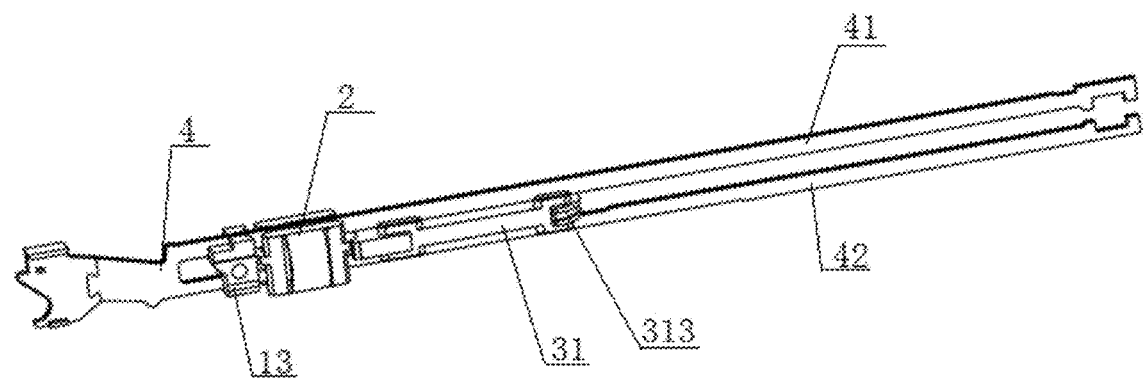
FIG. 10 is an assembled structure schematic diagram of a cutting blade assembly and other components according to one embodiment of the present invention.

In conjunction with what are shown in FIGS. 8 and 10, the cutting blade assembly 4 comprises a cutting blade assembly upper sheet 41 and a cutting blade assembly lower sheet 42, wherein the cutting blade assembly upper sheet 41 and the cutting blade assembly lower sheet 42 respectively and sequentially penetrate through the upper part and the lower part of the inner core connection block 31, the turning connection block 2 and the stapler anvil positioning piece 13, and are connected into one piece at the front end.

Specifically, as shown in FIG. 9, the upper surface and the lower surface of the inner core connection block 31 are respectively provided with a plurality of protruding snap-position steps 312, and an accommodating space for the upper sheet 41 of the cutting blade assembly or the lower sheet 42 of the cutting blade assembly is respectively formed among the plurality of protruding snap-position steps 312; the inner core shell comprises an inner core upper cover 32 and an inner core lower cover 33, and the inner core connection block 31 can be connected to the inner core upper cover 32 and the inner core lower cover 33 by snap-position steps 312.

Figure 11:
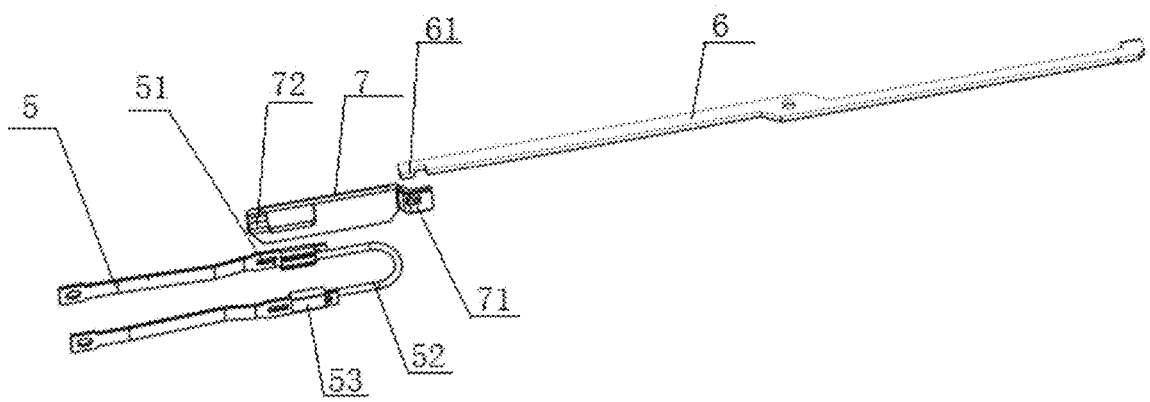
FIG. 11 is a schematic diagram of partial explosion structure of a bendable endoscopic linear cutting anastomat assembly according to one embodiment of the present invention (bending control part).

In conjunction with what is shown in FIG. 11, the push-pull rod 6 can be connected to the left and right bending sheet 5 by an intermediate connection piece, and the intermediate connection piece is a push-pull block 7, the push-pull rod 6 is mounted in a push-pull block hole 71 provided at the rear of the push-pull block 7 by a fixing boss 61 provided at the front thereof; and the push-pull block 7 is mounted in a fixing hole 51 provided at the left side or the right side of the left and right bending sheet 5 via a push-pull block shaft 72 provided at the front thereof.

The left and right bending sheet 5 in the above-mentioned bending control part can also be connected in other flexible ways besides the sheet form, for example the left and right bending sheet 5 can be completely replaced by a flexible steel wire rope. Alternatively, as shown in FIG. 11, the bending part 52 of the rear of the left and right bending sheet 5 is replaced with a flexible steel wire rope, and the flexible steel wire rope and the front part of the left and right bending sheet are press-fitted by a connection ring 53.

The present embodiment further provides a bendable endoscopic linear cutting anastomat, comprising a handle and an endoscopic linear cutting anastomat assembly connected to the front end of the handle, wherein the endoscopic linear cutting anastomat assembly preferably adopts the above-mentioned endoscopic linear cutting anastomat assembly.

When in surgical operation, the bendable endoscopic linear cutting anastomat enters the thoracic cavity or the abdominal cavity by a trocar in a linear state, the control bending mechanism on the handle outside the body controls the anastomat jaw to bend to a certain angle, and performs a series of operations such as clamping, transversely cutting and anastomosing on the surgical site. By means of arranging the dual rotation centers, the bending radius of the cutting blade is increased, the firing force during use is effectively reduced and a doctor can obtain a better operation hand feeling; the left and right flexible bending sheet is reversed, so that the left and right bending sheet can be always kept as a pulling process, thereby preventing the reduction of a force arm in the bending process, and the moment is stable. The above-mentioned arrangement also has a large bending angle at the same time, so that a doctor has a better operation space, and is suitable for medical treatment under more complex clinical conditions.

The foregoing description is merely preferred embodiments of the present invention, but is not intended to limit the present invention in any form. It will be understood by those skilled in the art may make some simple modifications, equivalent variations or modifications by using the above-disclosed technical content, which all belong to the protection scope of the present invention.

The invention claimed is:

1. A bendable endoscopic linear cutting anastomat assembly, comprising an anastomat jaw, a turning connection block, an assembly inner core, a cutting blade assembly, a left and right bending sheet comprising a left side and a right side connected by a bending part; and a push-pull rod; wherein the assembly inner core comprises an inner core shell and an inner core connection block fixedly mounted in the inner core shell;
   wherein a front end of the turning connection block is hinged to a rear end of the anastomat jaw, a first vertical rotation shaft is located at a first hinge to provide a first vertical rotation axis, a rear end of the turning connection block is hinged to a front end of the inner core connection block, a second vertical rotation shaft is located at a second hinge to provide a second vertical rotation axis, the cutting blade assembly penetrates through the inner core connection block, the turning connection block and the anastomat jaw, and is configured to slide forwards and backwards;
   wherein the left side or the right side of the left and right bending sheet is connected to a front end of the push-pull rod, and is configured to drive the anastomat jaw to bend left and right around the first vertical rotation axis and the second vertical rotation axis under the push-pull action of the push-pull rod as the bending part slides around the inner core connection block.

2. The bendable endoscopic linear cutting anastomat assembly according to claim 1, wherein the left and right bending sheet is U-shaped, and two free ends at a front end of the left and right bending sheet penetrate through the turning connection block from the rear to the front and are then fixedly connected to the rear end of the anastomat jaw.

3. The bendable endoscopic linear cutting anastomat assembly according to claim 2, wherein the anastomat jaw comprises a staple cartridge assembly located at an upper part and a stapler anvil connected to the staple cartridge assembly and located at a lower part, and further comprises a stapler anvil positioning piece located at an inner side of a rear part of the stapler anvil;
   the free ends of the left and right bending sheet are fixedly connected between the stapler anvil positioning piece and the rear part of the stapler anvil via a transversely connected pin, and the cutting blade assembly penetrates through the stapler anvil positioning piece.

4. The bendable endoscopic linear cutting anastomat assembly according to claim 3, wherein the turning connection block is connected to a positioning block connection shaft provided on the stapler anvil positioning piece via a vertical positioning block connection hole provided at the front end of the turning connection block; the turning connection block is connected to an inner core connection shaft provided at the front end of the inner core connection block via a vertical inner core connection block positioning hole provided at the rear end of the turning connection block.

5. The bendable endoscopic linear cutting anastomat assembly according to claim 3, wherein the cutting blade assembly comprises a cutting blade assembly upper sheet and a cutting blade assembly lower sheet, and the cutting blade assembly upper sheet and the cutting blade assembly lower sheet respectively and sequentially penetrate through the inner core connection block, the turning connection block, and an upper part and a lower part of the stapler anvil positioning piece, and are connected into one piece at a front end of the cutting blade assembly.

6. The bendable endoscopic linear cutting anastomat assembly according to claim 5, wherein a plurality of protruding snap-position steps are respectively provided on an upper surface and a lower surface of the inner core connection block, and an accommodating space for the cutting blade assembly upper sheet or the cutting blade assembly lower sheet is respectively formed among the plurality of protruding snap-position steps; the inner core shell comprises an inner core upper cover and an inner core lower cover, and the inner core connection block is connected to the inner core upper cover and the inner core lower cover by a snap-position step.

7. The bendable endoscopic linear cutting anastomat assembly according to claim 2, wherein a rear end of the inner core connection block is provided with a U-shaped groove, and an inner side of the bending part of the left and right bending sheet is fitted within the U-shaped groove.

8. The bendable endoscopic linear cutting anastomat assembly according to claim 2, wherein the bending part of the left and right bending sheet is-a flexible steel wire rope, and the flexible steel wire rope and a front part of the left and right bending sheet are press-fitted by a connection ring;

or the left and right bending sheet is the flexible steel wire rope.

9. The bendable endoscopic linear cutting anastomat assembly according to claim 1, wherein a left side face and a right side face of the turning connection block are respectively provided with a left and right bending sheet penetration opening, and a connection end of the push-pull rod and the left and right bending sheet is located at a rear end of the left and right bending sheet penetration opening;

the anastomat assembly further comprises a push-pull block, the push-pull rod is fitted into a push-pull block hole provided at a rear part of the push-pull block by a fixing boss provided at a front part of the push-pull rod, the push-pull block is fitted into a fixing hole provided at the left side or the right side of the left and right bending sheet via a push-pull block shaft provided at a front part of the push-pull block.

10. A bendable endoscopic linear cutting anastomat apparatus, comprising a handle and a bendable endoscopic linear cutting anastomat assembly connected to a front end of the handle, wherein the bendable endoscopic linear cutting anastomat assembly comprises:

an anastomat jaw, a turning connection block, an assembly inner core, a cutting blade assembly, a left and right bending sheet comprising a left side and a right side connected by a bending part; and a push-pull rod; wherein the assembly inner core comprises an inner core shell and an inner core connection block fixedly mounted in the inner core shell;

wherein a front end of the turning connection block is hinged to a rear end of the anastomat jaw, a first vertical rotation shaft is located at a first hinge to provide a first vertical rotation axis, a rear end of the turning connection block is hinged to a front end of the inner core connection block, a second vertical rotation shaft is located at a second hinge to provide a second vertical rotation axis, the cutting blade assembly penetrates through the inner core connection block, the turning connection block and the anastomat jaw, and is configured to slide forwards and backwards;

wherein the left side or the right side of the left and right bending sheet is connected to a front end of the push-pull rod, and is configured to drive the anastomat jaw to bend left and right around the first vertical rotation axis and the second vertical rotation axis under the push-pull action of the push-pull rod as the bending part slides around the inner core connection block.

* * * * *